(12) United States Patent
Fisher et al.

(10) Patent No.: US 8,206,392 B2
(45) Date of Patent: Jun. 26, 2012

(54) SURGICAL SAW DEVICE AND METHOD OF MANUFACTURE

(75) Inventors: Michael G. Fisher, Folsom, CA (US); John Anes, Folsom, CA (US)

(73) Assignee: Synvasive Technology, Inc., El Dorado Hills, CA (US)

( * ) Notice: Subject to any disclaimer, the term of this patent is extended or adjusted under 35 U.S.C. 154(b) by 451 days.

(21) Appl. No.: 12/603,396

(22) Filed: Oct. 21, 2009

(65) Prior Publication Data
US 2011/0092975 A1   Apr. 21, 2011

(51) Int. Cl.
*A61B 17/00* (2006.01)
(52) U.S. Cl. .......... 606/82; 606/176; 606/177; 606/178
(58) Field of Classification Search .......... 606/79, 606/82, 84, 167, 170, 171, 176, 177, 178; 30/392–394, 501–503.5, 329, 337, 339, 340, 30/342, 344
See application file for complete search history.

(56) References Cited

U.S. PATENT DOCUMENTS

| | | | |
|---|---|---|---|
| D3,994 S | 4/1870 | Moore | D8/20 |
| D4,255 S | 7/1870 | Rhodes | D8/20 |
| D4,497 S | 11/1870 | Rhodes | D8/20 |
| D4,706 S | 3/1871 | Kidd | D8/20 |
| D5,226 S | 8/1871 | Miller | D8/20 |
| 3,016,932 A | 1/1962 | Jacobson | 30/369 |
| 3,905,374 A | 9/1975 | Winter | 606/178 |
| 4,584,999 A | 4/1986 | Arnegger | 606/178 |
| 4,934,056 A | 6/1990 | Leini | 30/369 |
| 4,979,305 A * | 12/1990 | Leini | 30/369 |
| 5,306,285 A | 4/1994 | Miller et al. | 606/177 |
| 5,681,314 A | 10/1997 | Derouin et al. | 606/79 |
| 5,725,530 A | 3/1998 | Popken | 606/82 |
| 5,735,866 A | 4/1998 | Adams | 606/178 |
| 5,916,218 A | 6/1999 | Hagen | 606/82 |
| 6,007,541 A | 12/1999 | Scott | 606/82 |
| 6,063,083 A | 5/2000 | Duong-Van | 606/45 |
| 6,503,253 B1 | 1/2003 | Fletcher | 606/79 |
| 6,770,071 B2 | 8/2004 | Woloszko | 606/41 |
| 6,857,192 B1 | 2/2005 | Summers et al. | 30/294 |
| 7,060,072 B2 | 6/2006 | Wolff et al. | 606/84 |
| D525,707 S | 7/2006 | Kullmer et al. | D24/146 |
| D552,239 S | 10/2007 | Wolff | D24/147 |
| 7,322,985 B2 | 1/2008 | Lee | 606/71 |
| D576,729 S | 9/2008 | Tanaka et al. | D24/144 |
| D586,633 S | 2/2009 | Taylor et al. | D8/20 |
| D622,383 S | 8/2010 | Fisher | D24/146 |
| 7,901,424 B2 | 3/2011 | Fletcher | 606/176 |
| 2003/0014067 A1 | 1/2003 | Kullmer et al. | 606/172 |
| 2005/0245935 A1 | 11/2005 | Casey et al. | 606/82 |

OTHER PUBLICATIONS

PCT International Search Report and Written Opinion for PCT Application No. PCT/US2009/061549 mailed on Oct. 29, 2010.

* cited by examiner

*Primary Examiner* — Andrew Yang
(74) *Attorney, Agent, or Firm* — Knobbe Martens Olson & Bear LLP

(57) ABSTRACT

A surgical saw includes a shaft, a first saw blade mounted on the shaft, a second saw blade mounted on the shaft parallel to the first saw blade, the first saw blade having a first tooth having two distal tips, and the second saw blade having a second tooth with a distal tip, the second tooth bent towards the first saw blade and the distal tip of the second tooth aligned with a centerline between the two distal tips of the first tooth.

35 Claims, 11 Drawing Sheets

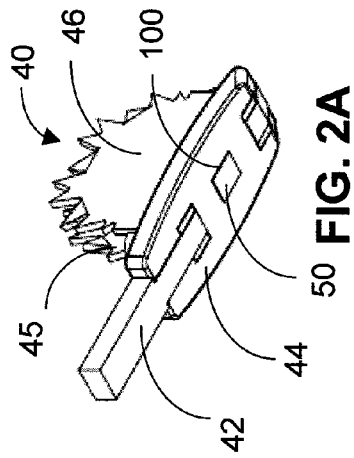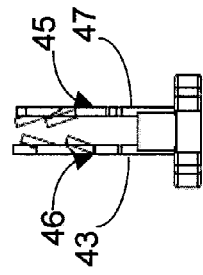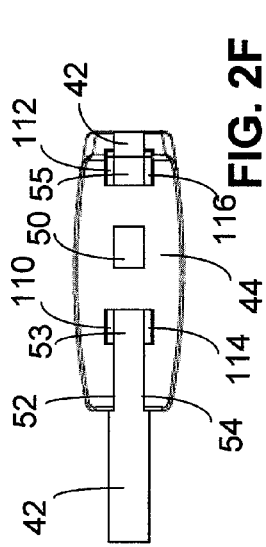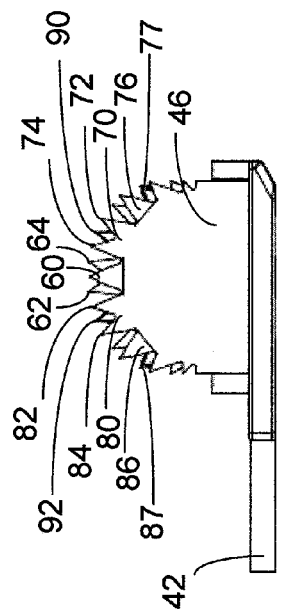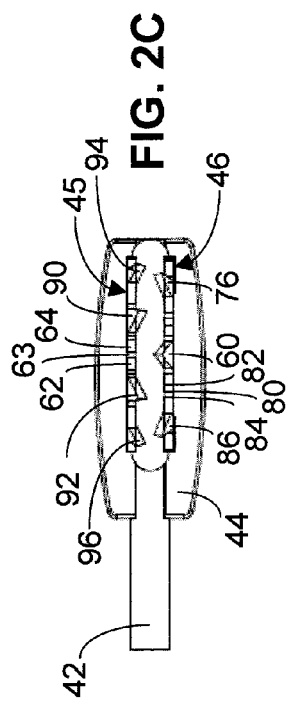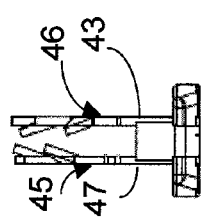

| PROVIDING A FIRST SAW BLADE HAVING A FIRST SAW BODY HAVING A FIRST THICKNESS AND HAVING TEETH ON A DISTAL END OF THE FIRST SAW BODY | 400 |
|---|---|

| PROVIDING A SECOND SAW BLADE HAVING A SECOND SAW BODY HAVING A SECOND THICKNESS AND HAVING TEETH ON A DISTAL END OF THE SECOND SAW BODY | 402 |
|---|---|

| PROVIDING A SHAFT HAVING A THIRD THICKNESS BETWEEN A FIRST SIDE OF THE SHAFT AND A SECOND SIDE OF THE SHAFT | 404 |
|---|---|

| PROVIDING A RETAINER HAVING A SLOT HAVING A WIDTH EQUAL TO THE SUM OF THE FIRST, SECOND AND THIRD THICKNESSES | 406 |
|---|---|

| PLACING THE FIRST SAW BLADE ON THE FIRST SIDE OF THE SHAFT | 408 |
|---|---|

| PLACING THE SECOND SAW BLADE ON THE SECOND SIDE OF THE SHAFT | 410 |
|---|---|

FIG. 6A

| MOUNTING THE RETAINER ON THE SHAFT SO THAT THE FIRST SAW BLADE FITS WITHIN THE SLOT ON THE RETAINER AND SO THAT THE SECOND SAW BLADE FITS WITHIN THE SLOT ON THE RETAINER WITH THE SHAFT BETWEEN THE FIRST AND SECOND SAW BLADES | 412 |
|---|---|
| ATTACHING THE RETAINER TO THE SHAFT AND THE RETAINER TO THE FIRST SAW BLADE AND TO THE SECOND SAW BLADE. | 414 |

FIG. 6B

| PROVIDING A SHAFT | 600 |

| MOUNTING A FIRST SAW BLADE ON THE SHAFT | 602 |

| MOUNTING A SECOND SAW BLADE ON THE SHAFT PARALLEL TO THE FIRST SAW BLADE, THE FIRST SAW BLADE HAVING A FIRST TOOTH HAVING TWO DISTAL TIPS, AND THE SECOND SAW BLADE HAVING A SECOND TOOTH WITH A DISTAL TIP, THE SECOND TOOTH BENT TOWARDS THE FIRST SAW BLADE AND THE DISTAL TIP OF THE SECOND TOOTH ALIGNED WITH A CENTERLINE BETWEEN THE TWO DISTAL TIPS OF THE FIRST TOOTH. | 604 |

FIG. 9

USING A SURGICAL SAW HAVING A SHAFT, A FIRST SAW BLADE MOUNTED ON THE SHAFT, A SECOND SAW BLADE MOUNTING ON THE SHAFT PARALLEL TO THE FIRST SAW BLADE, WHEREIN THE FIRST SAW BLADE HAS A FIRST TOOTH HAVING TWO DISTAL TIPS, AND
THE SECOND SAW BLADE HAS A SECOND TOOTH WITH A DISTAL TIP, THE SECOND TOOTH BENT TOWARDS THE FIRST SAW BLADE AND THE DISTAL TIP OF THE SECOND TOOTH ALIGNED WITH A CENTERLINE BETWEEN THE TWO DISTAL TIPS OF THE FIRST TOOTH.

SURGICAL SAW DEVICE AND METHOD OF MANUFACTURE

FIELD

This disclosure relates to surgical saw devices and methods of making surgical saw devices for cutting bone during surgery, and in particular to surgical saw blades adapted to be operatively coupled to powered surgical instruments.

BACKGROUND

Powered reciprocating saws with coupled bone cutting reciprocating surgical saw blades are widely used in orthopedic surgery. Typically, reciprocating surgical saw blades are used to form longitudinal cuts in bone, in line with the reciprocating action of a surgical reciprocating motor. These surgical reciprocating motors typically operate at speeds from 8,000 cycles per minute to up to approximately 16,000 cycles per minute, and have a stroke or "excursion" of approximately 3 mm-6 mm. A reciprocating surgical saw blade typically includes a proximal end coupled to the coupling member of the surgical reciprocating motor, and a distal end with a cutting means including an array of bone cutting teeth. The dimensions of a cutting means of a reciprocating surgical saw blade typically range from 0.38 mm to 1.47 mm in thickness, from 5 mm to 15 mm in height, and from 12 mm to 90 mm in length.

The cutting means of reciprocating surgical saw blades are typically arrayed parallel to the longitudinal axis of the reciprocating surgical saw blade and parallel with the reciprocating motion of the powered surgical saw. In some instances, the cutting means may include bone cutting teeth arrayed upon a projection perpendicular to and extending away from the longitudinal axis of the reciprocating surgical saw blade. In other instances, there may be more than one cutting means.

Typically, teeth arrayed along the cutting means of reciprocating surgical saw blades are spaced apart (pitch between the teeth) in such a manner that anywhere from 4 to 12 teeth would engage a bone within the excursion of a single complete reciprocating cycle of the powered surgical saw. In other words, the distance between the teeth is typically always less than the stroke or excursion of the powered surgical saw. This arrangement of teeth distributes the work-load among more teeth, reducing the chip load placed upon any individual tooth, and more importantly reduces the possibility of placing undue stress or heat upon the bone being cut. Further to mitigate placing undue stress or heat upon the bone being cut by reciprocating surgical saw blades, such blades are typically quite thin with a medium or fine pitch between the teeth.

Reciprocating surgical saw blades with cutting means projecting perpendicular to and extending away from the longitudinal axis of the reciprocating surgical saw blade are often used to perform closed bone cuts wherein the kerf, the dimensions of the saw cut, created by the reciprocating surgical saw blade, is closed on all 4 sides of the bone cut, such that there is no entry slot or exit slot. As a result, in surgical applications requiring bone cuts with such closed profiles, additional stress is placed upon the bone being cut, because the reciprocating surgical saw blade runs up against a vertical wall of bone as the reciprocating surgical saw blade is fed downwardly into the closed slot and reciprocated by advancing and retracting within the closed slot.

Surgical applications calling for closed profile bone cutting are additionally complicated in that the width of the kerf of the closed profile is typically up to 6× wider than the width of the cutting means of a typical reciprocating surgical saw blade. Perpendicular protruding cutting blades are often used to place closed slots in bone to receive a stabilizing feature on a prosthetic orthopedic implant, which is critical to the long-term stability and success of that implant. However, simply widening the cutting means to 6× its typical width would place additional undue stress on the bone being cut, to the point of possible fracture of the bone. As such, in surgical applications calling for closed profile bone cutting, in order to reduce the stress placed upon the bone, reciprocating surgical saw blades with two parallel cutting means are typically used. Such a surgical saw blade 10, is shown in FIGS. 1A-1C, in accordance with the prior art. While stress being placed upon the bone may be reduced by using reciprocating surgical saw blades such as those of FIGS. 1A-1C, other surgical objectives may not be obtained. As an example, if the thicknesses of the two parallel cutting means 16 and 20, as shown in FIG. 1B, are acceptable in that they do not place undue stress on the bone being cut, each of the parallel cutting means 16 and 20 may not be wide enough to generate a kerf wide enough to receive the stabilizing feature of various implants. Also, if the thicknesses of the two parallel cutting means 16 and 20 are acceptable in that they do not place undue stress on the bone being cut and are simply spaced apart to the point that they are wide enough to generate a kerf wide enough to receive the stabilizing feature of various implants, there may be a ridge of bone left between the two parallel cutting means 16 and 20. The resulting bone ridge is especially difficult to remove when performing closed profile bone cutting.

What is needed is a reciprocating surgical saw blade suitable for operation with a surgical reciprocating motor that can perform closed profile bone cutting. The resulting kerf cut by the reciprocating surgical saw blade needs to be long enough and wide enough to receive the stabilizing features of an orthopedic implant, and the cutting means of the reciprocating surgical saw blade needs to form the kerf without placing undue stress on the bone being cut. The embodiments of the present disclosure answer these and other needs.

SUMMARY

In a first embodiment disclosed herein, a surgical saw comprises a shaft, a first saw blade mounted on the shaft, a second saw blade mounted on the shaft parallel to the first saw blade, the first saw blade having a first tooth having two distal tips, and the second saw blade having a second tooth with a distal tip, the second tooth bent towards the first saw blade and the distal tip of the second tooth aligned with a centerline between the two distal tips of the first tooth.

In another embodiment disclosed herein, a surgical saw comprises a shaft, a first saw blade mounted on the shaft, a second saw blade mounted on the shaft parallel to the first saw blade, the first saw blade having a first type tooth with a single distal tip that is bent towards the second saw blade, the first type tooth arranged in the middle of the first saw blade and the distal tip of the first type tooth aligned with a center line between two distal tips of a second type tooth having two distal tips on the second saw blade, the first saw blade having a second type tooth on each side of the middle first type tooth on the first saw blade, the second type tooth having two distal tips, the first saw blade having a first type tooth having one distal tip that is bent toward the second saw blade on a side of each second type tooth on the first saw blade, the second saw blade having the second type tooth having two distal tips arranged in the middle of the second saw blade, and the second saw blade having a plurality of teeth on either side of the middle second type tooth, the plurality of teeth alternating between a first type tooth having a single distal tip that is bent towards the first saw blade and a third type tooth having a single distal tip that is not bent.

In yet another embodiment disclosed herein, a surgical saw comprises a first saw blade having a first saw body having a first thickness, a second saw blade having a second saw body having a second thickness, a shaft having a third thickness between a first side of the shaft and a second side of the shaft, a retainer having a slot having a width equal to the sum of the first, second and third thicknesses, wherein the first saw blade is mounted on the first side of the shaft and the second saw blade is mounted on the second side of the shaft, and wherein the retainer is attached to the shaft and the first and second saw blade such that the first saw blade and the second saw blade on the first side and the second side of the shaft, respectively, fit within the slot on the retainer.

In still another embodiment disclosed herein, a method of manufacturing a surgical saw comprises providing a first saw blade having a first saw body having a first thickness and having teeth on a distal end of the first saw body, providing a second saw blade having a second saw body having a second thickness and having teeth on a distal end of the second saw body, providing a shaft having a third thickness between a first side of the shaft and a second side of the shaft, providing a retainer having a slot having a width equal to the sum of the first, second and third thicknesses, placing the first saw blade on the first side of the shaft, placing the second saw blade on the second side of the shaft, mounting the retainer on the shaft so that the first saw blade fits within the slot on the retainer and so that the second saw blade fits within the slot on the retainer with the shaft between the first and second saw blades, and attaching the retainer to the shaft and the retainer to the first saw blade and to the second saw blade.

In still another embodiment disclosed herein a method of forming a surgical saw comprises providing a shaft, mounting a first saw blade on the shaft, and mounting a second saw blade on the shaft parallel to the first saw blade, the first saw blade having a first tooth having two distal tips, and the second saw blade having a second tooth with a distal tip, the second tooth bent towards the first saw blade and the distal tip of the second tooth aligned with a centerline between the two distal tips of the first tooth.

In yet another embodiment disclosed herein a method of performing surgery comprises using a surgical saw having a shaft, a first saw blade mounted on the shaft, a second saw blade mounting on the shaft parallel to the first saw blade, wherein the first saw blade has a first tooth having two distal tips, and the second saw blade has a second tooth with a distal tip, the second tooth bent towards the first saw blade and the distal tip of the second tooth aligned with a centerline between the two distal tips of the first tooth.

These and other features and advantages will become further apparent from the detailed description and accompanying figures that follow. In the figures and description, numerals indicate the various features, like numerals referring to like features throughout both the drawings and the description.

BRIEF DESCRIPTION OF THE DRAWINGS

FIGS. 2A-2F show a perspective view, a side elevation view, a bottom view, a rear view, a front view, and a top view, respectively, of a surgical saw in accordance with the present disclosure;

FIGS. 6A and 6B are block diagrams of a method of manufacturing a surgical saw in accordance with the present disclosure;

FIG. 9 is a block diagram of a method of manufacturing a surgical saw in accordance with the present disclosure; and FIG. 10 is a block diagram of a method of performing surgery in accordance with the present disclosure.

DETAILED DESCRIPTION

In the following description, numerous specific details are set forth to clearly describe various specific embodiments disclosed herein. One skilled in the art, however, will understand that the presently claimed invention may be practiced without all of the specific details discussed below. In other instances, well known features have not been described so as not to obscure the invention.

Figures 1A, 1B, 1C, 1D:
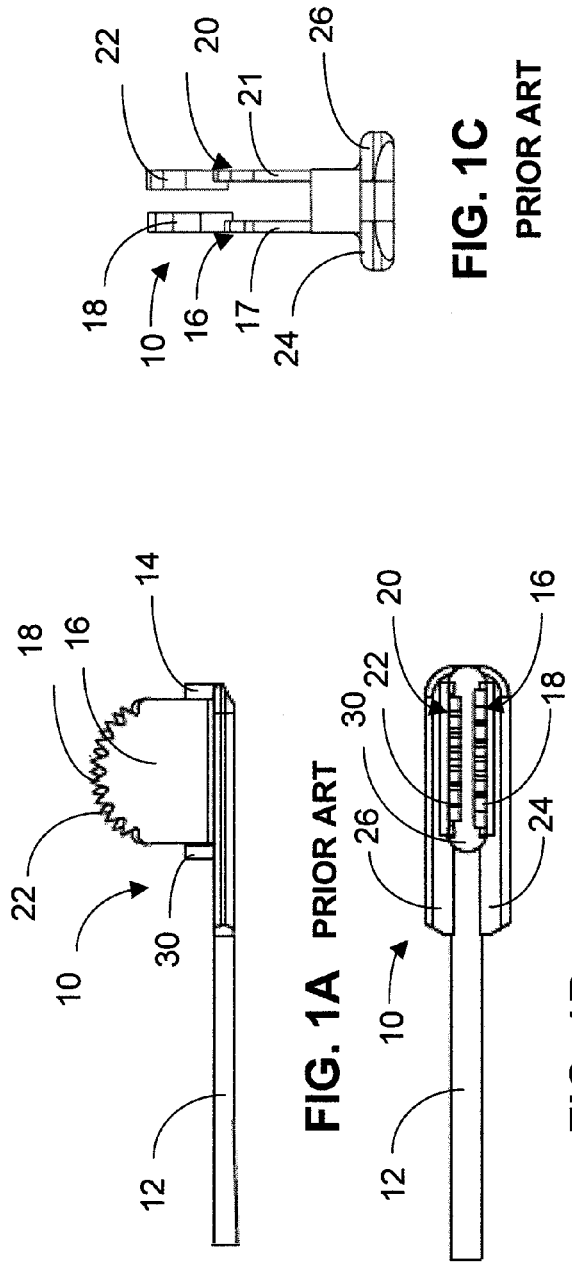
FIGS. 1A to 1C show a side elevation view, a top view and a front view, respectively, of a surgical saw in accordance with the prior art.
FIG. 1D illustrates a method of fabricating a surgical saw in accordance with the prior art.

Referring now to FIGS. 1A to 1C, a surgical saw 10 is shown for use with a surgical reciprocating motor (not shown) in accordance with the prior art. FIG. 1A shows a side elevation view of the surgical saw 10, showing the shaft 12, which is typically coupled to a surgical reciprocating motor, and a saw blade 16 with teeth 18 projecting perpendicular to the shaft. In this view only the teeth 22 of the parallel saw blade 20 can be seen. The shaft 12 has a protrusion 30 with a distal end 14 extending between the saw blades 16 and 20. FIG. 1B is a top view of the surgical saw 10, which shows the two parallel saw blades 16 and 20, having teeth 18 and 22, respectively. FIG. 1C is a front view the surgical saw 10 and illustrates the two saw blades 16 and 20 projecting perpendicular from the shaft 12.

FIG. 1D illustrates a method of fabricating the surgical saw of FIGS. 1A-1C in accordance with the prior art. First of all the shaft 12 is formed. As is evident in FIG. 1D to form the shaft 12 with protrusion 30 formed with recesses 32 requires complicated cutting and milling. To form the saw blades 16 and 20 also requires complicated cutting and milling to form teeth 18 and 22, respectively, and to form wings 24 and 26, respectively. The wings 24 and 26 of the saw blades 16 and 20, respectively, are aligned with recesses 32 and then welded to the shaft 12 to complete the assembly of the surgical saw 10.

In FIG. 1C it is shown that in this prior art surgical saw 10, that the bodies 17 and 21 of the saw blades 16 and 20, respectively, are thinner than the teeth 18 and 22, respectively. In the prior art the teeth may also have the same width as the body of the saw blade. As discussed above, the width of the teeth may be selected to form a kerf with a little or no bone ridge between where the teeth cut the bone when performing closed profile bone cutting, as well as other types of cuts. However, as also discussed above, wide teeth may result in undue stress being placed on the bone being cut.

Figure 3:
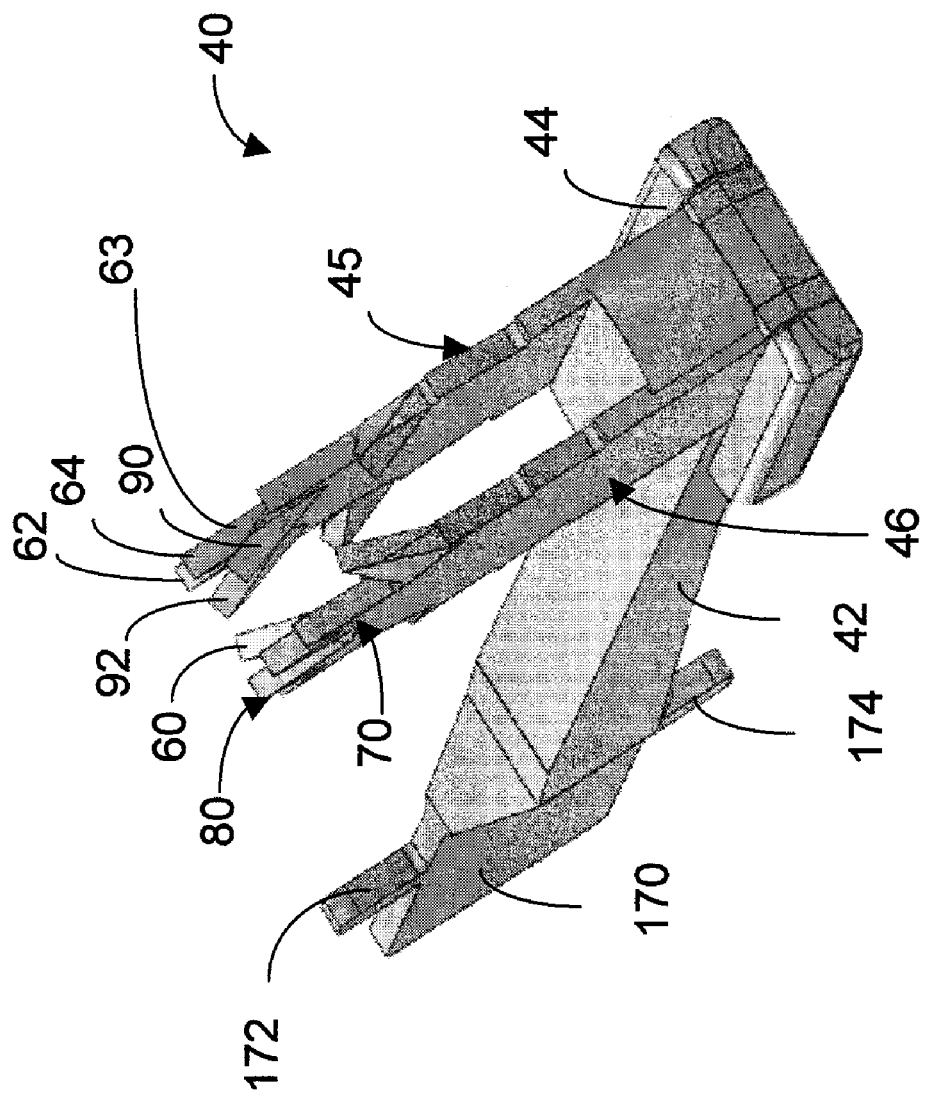
FIG. 3 shows another perspective view of a surgical saw in accordance with the present disclosure.

Referring now to FIGS. 2A to 2F, a surgical saw 40 in accordance with the present disclosure is shown. FIG. 2A is one perspective view of the surgical saw 40 and FIG. 3 is another perspective view of a surgical saw 40 in accordance with the present disclosure, which also shows the end of the surgical saw 170 and protrusions 172 and 174 for mounting the surgical saw 40 to a surgical reciprocating motor. Referring again to FIG. 2A, the surgical saw 40 has a shaft 42 and a retainer 44 upon which saw blades 45 and 46 are mounted as described further below. The retainer 44 may be attached to a boss 50 on the shaft 42.

FIG. 2B is a side elevational view of the surgical saw blade 40 showing further details of the teeth on each saw blade 45 and 46. As shown in FIG. 2B, the saw blades are parallel to one another.

The saw blade 46 has three types of teeth, a first type tooth with a single distal tip that is bent toward the parallel saw blade 45, a second type tooth with two distal tips that is not bent, and a third type tooth with a single distal tip that is not bent. The purpose of the first type tooth that is bent toward the parallel saw blade is to widen the cut or kerf. The purposes of the second and third type teeth are to create a cutting path and to help with down feeding of the saw blade into the cut. On saw blade 46 the middle tooth 60 is a first type tooth with a single distal tip and is bent toward saw blade 45 by an amount described below. On either side of tooth 60 are teeth 70 and 80 that are second type teeth that each have two distal tips 72, 74, and 82, 84, respectively, and are not bent. Teeth 70 and 80 may be described as fishtail teeth in that they have 2 distal tips. Going further away from the middle tooth 60, saw blade 46 has teeth 76 and 86, next to teeth 70 and 80, respectively. Teeth 76 and 86 are first type teeth with only one distal tip and are bent toward saw blade 45. Going even further away from the middle tooth the saw blade may have additional third type teeth each with a single distal tip that is not bent. In one embodiment the first type teeth and the third type teeth may have a shape of an isosceles triangle.

Also shown in FIG. 2B are the tips of teeth on saw blade 45. In the middle of saw blade 45 is a second type tooth 63 with two distal tips 62 and 64. On either side of tooth 63 are teeth 90 and 92, which are first type teeth with one distal tip bent toward the parallel saw blade, which is saw blade 46. Going further away from the middle tooth 63, saw blade 45 has third type teeth 77 and 87, next to teeth 90 and 92, respectively. Teeth 77 and 87 each have one distal tip that is not bent. Going even further away from the middle tooth 63, saw blade 45 has a first type tooth 94 and 96 next to teeth 77 and 87, respectively. Then saw blade 45 has third type teeth next to teeth 94 and 96, respectively.

FIGS. 2C-2F show a bottom view, a rear view, a front view, and a top view, respectively, of a surgical saw 40 in accordance with the present disclosure. FIGS. 2C-2E show that the first type teeth, including teeth 60, 76 and 86 on saw blade 46 are bent toward saw blade 45, and first type teeth 90, 92, 94 and 96 on saw blade 45 are bent toward saw blade 46. As shown in FIGS. 2D and 2E, the saw blade 46 has a saw body 43 which has a thickness and the teeth on saw blade 46, such as teeth 60, 70, 76, 80 and 86, are on a distal end of the saw body 43. In one embodiment the first type teeth, such as teeth 60, 76 and 86 on saw blade 46 are bent towards saw blade 45 by an amount not exceeding 150% of the thickness of the saw body 43. Similarly, the saw blade 45 has a saw body 47 which has a thickness and the teeth on saw blade 45, such as teeth 63, 90, 77, 94, 92, 87, and 96, are on a distal end of the saw body 47. The first type teeth, such as teeth 90, 92, 94 and 96 on the saw blade 45 are bent towards saw blade 46 by an amount not exceeding 150% of the thickness of the saw body 47. In another embodiment the distal tip of the bent middle tooth 60 on saw blade 46 has a height that is less that the height of the two distal tips of tooth 63 on saw blade 45. In another embodiment the distal tip of the bent middle tooth 60 on saw blade 46 is aligned such that the distal tip of tooth 60 is aligned with a centerline between the two distal tips 62 and 64 on second type tooth 63, as is best shown in FIG. 2B.

Figure 4:
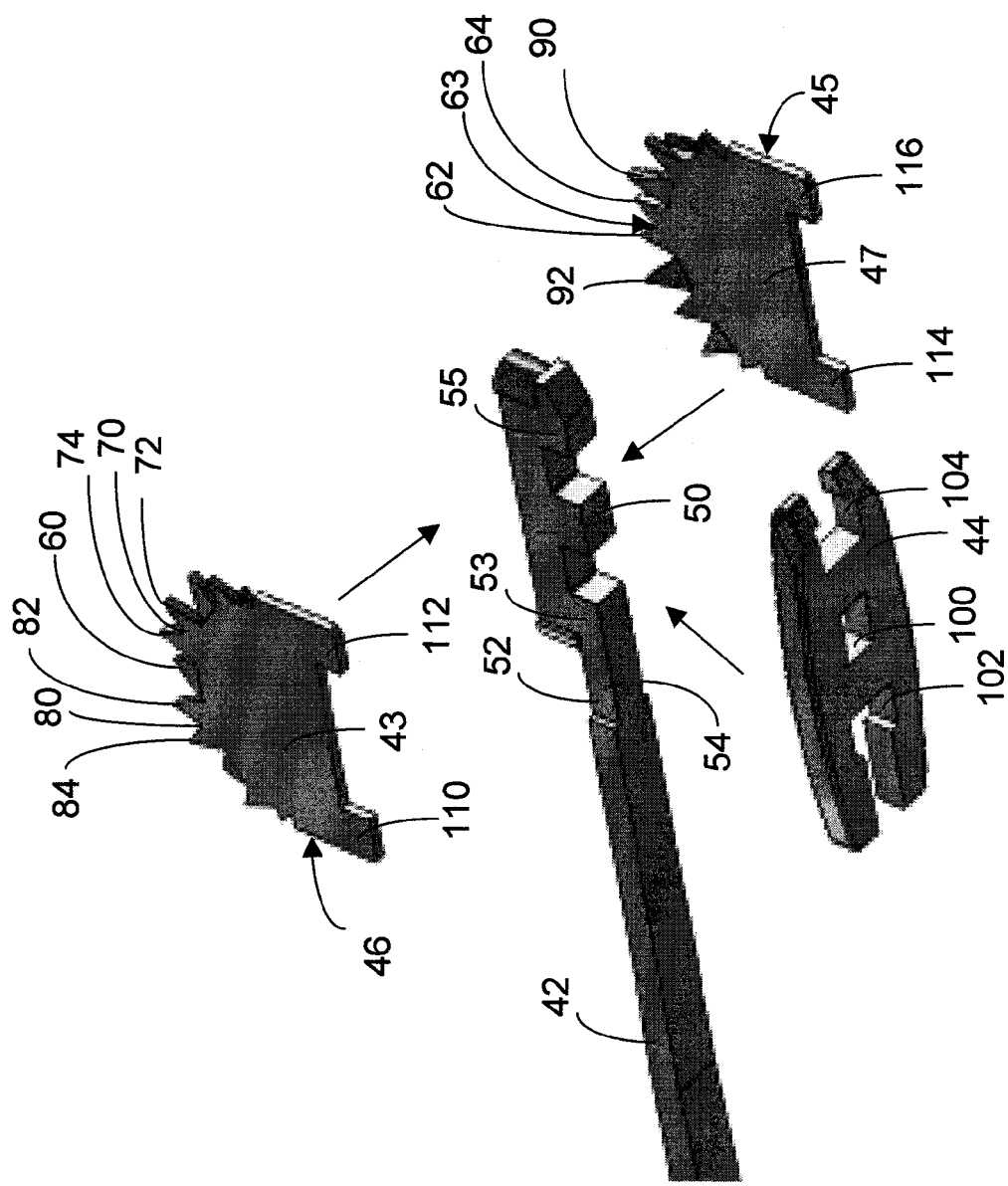
FIG. 4 illustrates a method of fabricating a surgical saw in accordance with the present disclosure.

The assembly of the surgical saw 40 is best understood in relation to FIG. 4, which shows a disassembled surgical saw. As shown in FIG. 4, tangs 110 and 112 are on the proximal end of saw blade 46, and tangs 114 and 116 are on the proximal end of saw blade 45. The shaft 42, as shown in FIG. 4, has recesses 52 and 54, which result in a thickness at areas 53 and 55. A boss 50 is also formed on shaft 42 between areas 53 and 55. FIG. 4 also shows retainer 44, which has slots 100, 102 and 104. As shown in FIG. 2F, when assembled the boss 50, which has a width, is fit into slot 100, which has a corresponding width. Also tang 110 on saw blade 46, area 53, and tang 114 on saw blade 45 are fit into slot 102, which has a width that is approximately the sum of the thicknesses of tang 110, area 53, and tang 114. Similarly, tang 112 on saw blade 46, area 55, and tang 116 on saw blade 45 are fit into slot 104, which has a width that is approximately the sum of the thicknesses of tang 112, area 55, and tang 116. Once the assembly of the boss 50 into slot 100, the assembly of tang 110 on saw blade 46, area 53, and tang 114 on saw blade 45 into slot 102, and the assembly of tang 112 on saw blade 46, area 55, and tang 116 on saw blade 45 into slot 104 are complete, simple attachment methods may be used to fasten saw blades 45 and 46, retainer 44, and shaft 42 together. The result is a surgical saw that is easier to fabricate and assemble than the prior art assembly as discussed above with reference to FIG. 1D.

Figure 5A:
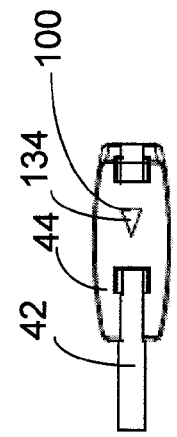
FIGS. 5A-5G show alternate bottom views of surgical saws in accordance with the present disclosure.
Figure 5B:
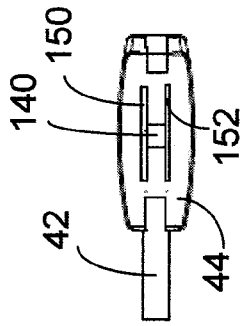
Figure 5C:
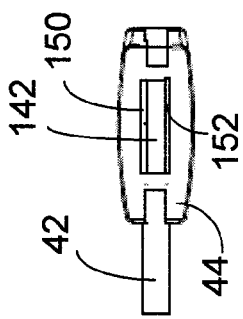
Figure 5D:
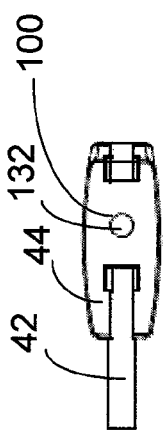
Figure 5E:
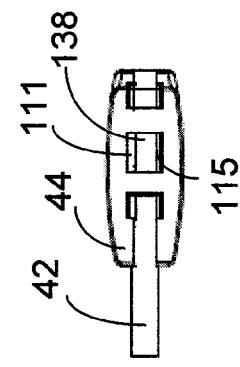
Figure 5F:
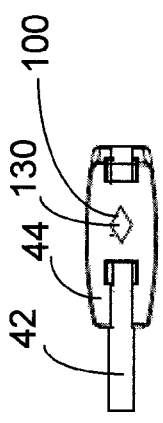
Figure 5G:
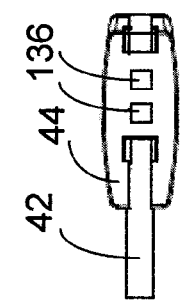

FIGS. 5A-5G show alternate bottom views of surgical saws formed in accordance with the present disclosure. FIG. 5A shows an alternate boss 130, which has a diamond form. In this embodiment the slot 100 has a matching diamond shape. FIG. 5B shows another boss 132, which has a circular form. In this embodiment the slot 100 has a matching circular shape. FIG. 5C shows another boss 134, which has a triangular form. In this embodiment the slot 100 has a matching triangular shape. FIG. 5D shows yet another boss 136 design, which in this design includes two rectangular forms. In this embodiment the slot 100 would be two rectangular matching slots. FIG. 5E shows yet another boss 138 design, which in this design has a rectangular form, but which is narrower than slot 100. The saw blades 45 and 46 each have an additional tang 111 and 115, respectively, which fit on either side of the boss 138 and fit into rectangular slot 100. FIG. 5F shows yet another boss 140, which in this design also has a rectangular form that is narrower than slot 100. The saw blades 45 and 46 each have one tang 150 and 152, respectively, which fit on either side of the boss 140, but are longer than the boss 140 and the slot 100 includes linear slits into which the longer tangs 150 and 152 fit. This design has the advantage that each saw blade needs to only have one tang, albeit a longer tang in order to ensure that the tang when welded to the retainer 44 and the shaft 42 is securely fastened. FIG. 5G shows yet another boss 142, which in this design also has a rectangular form that is narrower than slot 100. The saw blades 45 and 46 each have one tang 150 and 152, respectively, which fit on either side of the boss 142. In this embodiment, the boss 142 and the tangs 150 and 152 each have the same length, so the slot 100 may be rectangular. Similar to the embodiment of FIG. 5F, each of the saw blades 45 and 46 need only have one tang in the embodiment of FIG. 5G.

In another embodiment, saw blades 45 and 46 have no tangs but rather just have proximal ends 150 and 152 respectively, as shown in FIGS. 5F and 5G, that fit into the linear slits on FIG. 5F or on either side of boss 142 as shown in FIG. 5G.

FIGS. 6A and 6B are block diagrams of a method of manufacturing a surgical saw in accordance with the present disclosure. The method includes step 400 of providing a first saw blade 45 having a first saw body 47 having a first thickness and having teeth on a distal end of the first saw body 47, step 402 of providing a second saw blade 46 having a second saw body 43 having a second thickness and having teeth on a distal end of the second saw body 43, step 404 of providing a shaft having a third thickness between a first side of the shaft 52 and a second side of the shaft 54, step 406 of providing a retainer 44 having a slot 102 having a width equal to the sum of the first, second and third thicknesses, step 408 of placing the first saw blade 45 on the second side 54 of the shaft 42, step 410 of placing the second saw blade 46 on the first side 52 of the shaft 42, step 412 of mounting the retainer 44 on the shaft 42 so that the first saw blade 45 fits within the slot 100 on the retainer 44 and so that the second saw blade 46 fits within the slot 100 on the retainer 44 with the shaft 42 between the first and second saw blades, and step 414 of attaching the retainer 44 to the shaft 42 and the retainer 44 to the first saw blade and to the second saw blade.

The method of attaching may include welding, laser welding, brazing, gluing and any other attaching methods well known in the art. The method may also include steps of attaching the tangs on the saw blades to the retainer and the shaft.

Figure 7A:
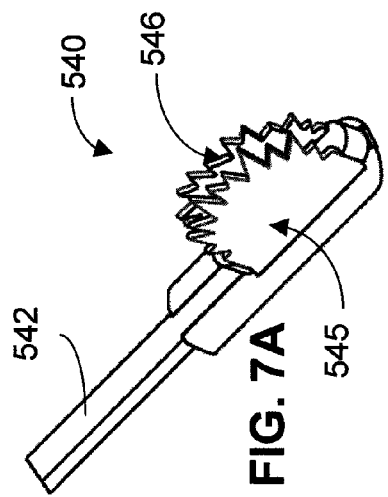
FIGS. 7A-7F show a perspective view, a side elevation view, a bottom view, a rear view, a front view, and a top view, respectively, of another surgical saw in accordance with the present disclosure.
Figure 7E:
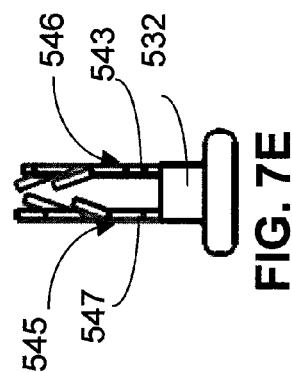
Figure 7F:
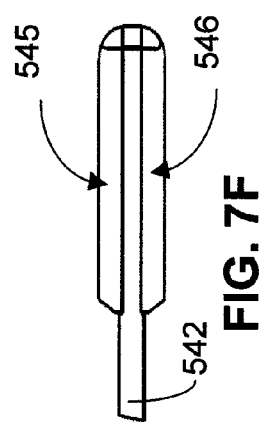
Figure 7B:
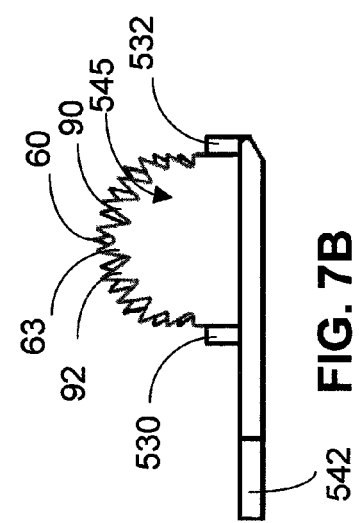

Referring now to FIGS. 7A to 7F, a surgical saw 540 in accordance with the present disclosure is shown. FIG. 7A is a perspective view of the surgical saw 540. The surgical saw 540 has a shaft 542 which can be attached to a motor. FIG. 7B is a side elevational view of the surgical saw blade 540 showing further details of the teeth on each saw blade 545 and 546. As shown in FIG. 2B, the saw blades are parallel to one another.

Figure 8:
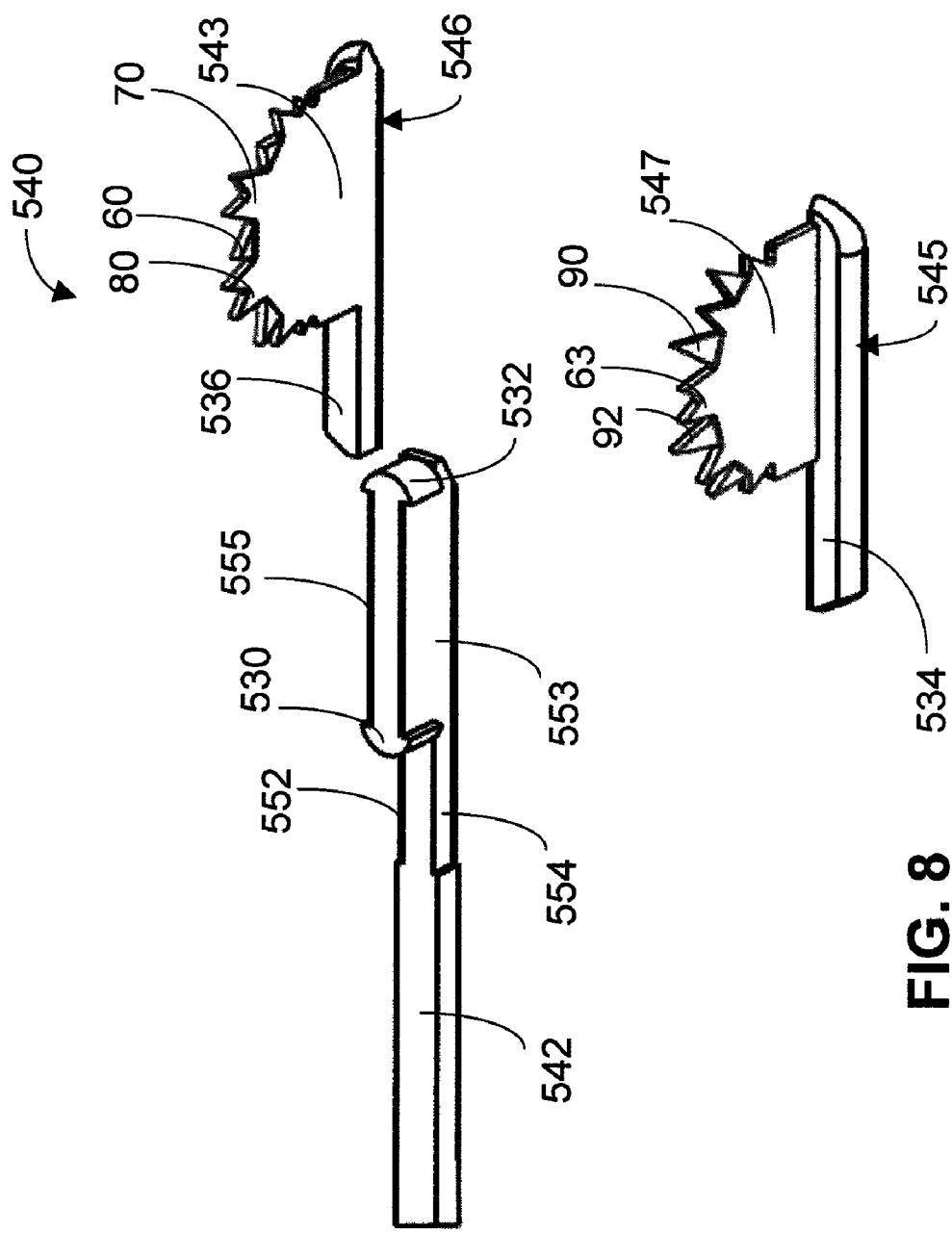
FIG. 8 shows another perspective view of a surgical saw in accordance with the present disclosure.

The saw blade 546 has three types of teeth that are arranged in the same way as the teeth on saw blade 46 described above. A first type tooth with a single distal tip that is bent toward the parallel saw blade 545, a second type tooth with two distal tips that is not bent, and a third type tooth with a single distal tip that is not bent. The purpose of the first type tooth that is bent toward the parallel saw blade is to widen the cut or kerf. The purposes of the second and third type teeth are to create a cutting path and to help with down feeding of the saw blade into the cut. On saw blade 546 the middle tooth 60 is a first type tooth with a single distal tip and is bent toward saw blade 545 by an amount described below. On either side of tooth 60 are teeth 70 and 80, as shown in FIG. 8, that are second type teeth that each have two distal tips and are not bent. Teeth 70 and 80 may be described as fishtail teeth in that they have 2 distal tips. Moving further away from the middle tooth the saw blade 546 has another first type tooth and then two third type teeth. In one embodiment the first type teeth and the third type teeth may have a shape of an isosceles triangle.

Also shown in FIG. 7B and FIG. 8 are the tips of teeth on saw blade 545 that has three types of teeth that are arranged in the same way as the teeth on saw blade 45 described above. In the middle of saw blade 545 is a second type tooth 63 with two distal tips. On either side of tooth 63 are teeth 90 and 92, which are first type teeth with one distal tip bent toward the parallel saw blade, which is saw blade 546. Going further away from the middle tooth 63, saw blade 45 has third type teeth which have a single distal tip that is not bent next to teeth 90 and 92, respectively. Going even further away from the middle tooth 63, saw blade 545 has first type teeth and then saw blade 45 has third type teeth, in the same manner as saw blade 45 described above.

Figure 7C:
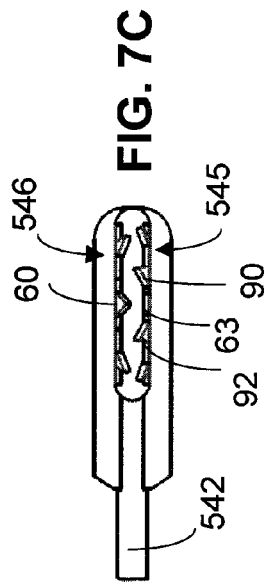
Figure 7D:
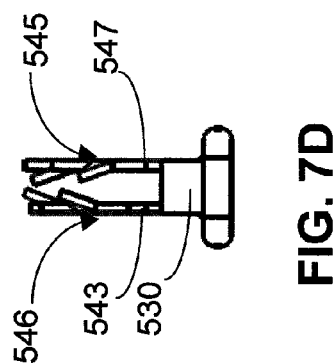

FIGS. 7C-7F show a bottom view, a rear view, a front view, and a top view, respectively, of surgical saw 540 in accordance with the present disclosure. FIGS. 7C-7E show that the first type teeth on saw blade 546 are bent toward saw blade 545, and first type teeth on saw blade 545 are bent toward saw blade 546. As shown in FIGS. 7D and 7E, the saw blade 546 has a saw body 543 which has a thickness. In one embodiment the first type teeth on saw blade 546 are bent towards saw blade 545 by an amount not exceeding 150% of the thickness of the saw body 543. Similarly, the saw blade 545 has a saw body 547 which has a thickness and the first type teeth on the saw blade 545 are bent towards saw blade 546 by an amount not exceeding 150% of the thickness of the saw body 547. In another embodiment the distal tip of the bent middle tooth 60 on saw blade 546 has a height that is less that the height of the two distal tips of tooth 63 on saw blade 545. In another embodiment the distal tip of the bent middle tooth 60 on saw blade 546 is aligned such that the distal tip of tooth 60 is aligned with a centerline between the two distal tips on second type tooth 63, as is best shown in FIG. 7B.

The assembly of the surgical saw 540 is best understood in relation to FIG. 8, which shows a disassembled surgical saw. As shown in FIG. 8, the shaft 542 has recesses 552 and 554, which extend to recesses 553 and 555, respectively. These recesses reduce the thickness of shaft 542 and provide mounting surfaces for saw blades 545 and 546. As shown in FIG. 8 the shaft 542 also has protrusions 530 and 532. The body 543 of saw blade 546 and the body 547 of saw blade 545 have a length which fits between the protrusions 530 and 532 when the surgical saw is assembled. The protrusions 530 and 532 extend outward from the shaft a distance that is approximately the thickness of the saw blade bodies 543 and 547. Saw blade 545 includes the saw body 547 with teeth on the distal end of the saw body 547, as discussed above, and the saw body 547 is integral with a stop guide 534 that fits along recess 554 and 553. Similarly, saw blade 546 includes the saw body 543 with teeth on the distal end of the saw body 543, as discussed above, and the saw body 543 is integral with a stop guide 536 that fits along recess 552 and 555.

When the saw blades 545 and 546 are fit within the recesses on shaft 542, simple attachment methods may be used to fasten saw blades 545 and 546 to shaft 542. The result is a surgical saw that is less costly to fabricate and assemble than the prior art assembly as discussed above with reference to FIG. 1D.

FIG. 9 is a block diagram of a method of manufacturing a surgical saw in accordance with the present disclosure and steps 600, 602 and 604 are in accordance with the above description of the surgical saw.

FIG. 10 is a block diagram of a method of performing surgery in accordance with the present disclosure and step 610 is using a surgical saw in accordance with the above description in surgery.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

The foregoing Detailed Description of exemplary and preferred embodiments is presented for purposes of illustration and disclosure in accordance with the requirements of the law. It is not intended to be exhaustive nor to limit the invention to the precise form(s) described, but only to enable others skilled in the art to understand how the invention may be suited for a particular use or implementation. The possibility of modifications and variations will be apparent to practitioners skilled in the art. No limitation is intended by the description of exemplary embodiments which may have included tolerances, feature dimensions, specific operating conditions, engineering specifications, or the like, and which may vary between implementations or with changes to the state of the art, and no limitation should be implied therefrom. Applicant has made this disclosure with respect to the current state of the art, but also contemplates advancements and that adaptations in the future may take into consideration of those advancements, namely in accordance with the then current state of the art. It is intended that the scope of the invention be defined by the Claims as written and equivalents as applicable. Reference to a claim element in the singular is not intended to mean "one and only one" unless explicitly so stated. Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising the step(s) of . . . ."

What is claimed is:

1. A surgical saw comprising:
   a shaft;
   a first saw blade mounted on the shaft;
   a second saw blade mounted on the shaft parallel to the first saw blade;
   the first saw blade having a first tooth having two distal tips; and
   the second saw blade having a second tooth with a distal tip, the second tooth bent towards the first saw blade and the distal tip of the second tooth aligned with a centerline between the two distal tips of the first tooth.

2. The surgical saw of claim 1 wherein the first tooth is symmetric about the center line between the two distal tips of the first tooth.

3. The surgical saw of claim 1 wherein the second tooth has a shape of an isosceles triangle.

4. The surgical saw of claim 1 wherein the second saw blade comprises:
   a saw body having a thickness;
   wherein the second tooth is on a distal end of the saw body and bent towards the first saw blade by an amount not exceeding 150% of the thickness of the saw body.

5. The surgical saw of claim 1 wherein the distal tip of the bent second tooth has less height than the two distal tips of the first tooth.

6. The surgical saw of claim 1 wherein:
   the first saw blade further comprises:
      a third tooth having a distal tip, the third tooth bent towards the second saw blade and on one side of the first tooth; and
      a fourth tooth having a distal tip, the fourth tooth bent towards the second saw blade and on a second side of the first tooth; and
   the second saw blade further comprises:
      a fifth tooth having two distal tips with a centerline between the two distal tips of the fifth tooth aligned with the distal tip of the third tooth; and
      a sixth tooth having two distal tips with a centerline between the two distal tips of the sixth tooth aligned with the distal tip of the fourth tooth.

7. The surgical saw of claim 6 wherein the third and fourth teeth each have a shape of an isosceles triangle.

8. The surgical saw of claim 6 wherein the first saw blade comprises:
   a saw body having a thickness;
   wherein the third and fourth teeth are each on a distal end of the saw body and bent towards the second saw blade by an amount not exceeding 150% of thickness of the saw body.

9. The surgical saw of claim 1 further comprising:
   a retainer having a slot;
   wherein:
      the first saw blade has a first saw body having a first thickness;
      the second saw blade having a second saw body having a second thickness;
      the shaft has a thickness between a first side of the shaft and a second side of the shaft; and
      the slot has a width equal to the sum of the first, second and third thicknesses;
      the first saw blade is mounted on the first side of the shaft and the second saw blade is mounted on the second side of the shaft; and
      the retainer is attached to the shaft and the first and second saw blade such that the first saw blade and the second saw blade on the first side and the second side of the shaft, respectively, fit within the slot on the retainer.

10. The surgical saw of claim 9 wherein:
    the shaft further comprises a boss;
    the retainer has a second slot having a thickness equal to the third thickness of the shaft; and
    the boss fits within the second slot and is attached to the shaft.

11. The surgical saw of claim 10 wherein the boss has a shape selected from a group comprising a rectangular shape, a diamond shape, a circular shape, and a triangular shape.

12. The surgical saw of claim 9 wherein:
    the first saw blade comprises a tang on the proximal end of the first saw blade; and
    the second saw blade comprises a tang on the proximal end of the second saw blade;
    wherein the retainer is attached to the shaft and the first and second saw blade such that the tang on the first saw blade and the tang on the second saw blade are mounted on the first side and the second side of the shaft, respectively, and fit within the slot on the retainer.

13. The surgical saw of claim 12 wherein:
    the first saw blade has a second tang;
    the second saw blade has a second tang; and
    the retainer has a second slot having a width equal to the sum of the first, second and third thicknesses;
    wherein the retainer is attached to the shaft and the first and second saw blade such that the second tang of the first saw blade and the second tang of the second saw blade on the first side and the second side of the shaft, respectively, fit within the slot on the retainer.

14. The surgical saw of claim 1 wherein:
    the first saw blade has a first stop guide on a proximal end;
    the second saw blade has a second stop guide on a proximal end;
    the shaft has a first recess on a first side of the shaft and a second recess on a second side of the shaft; and the first stop guide is mounted within the first recess and the second saw blade is mounted within the second recess.

15. The surgical saw of claim 14 wherein:
the first saw blade has a first saw body having a length;
the second saw blade has a second saw body having the length;
the shaft has a first and a second protrusion separated by the length; and
the first saw body and the second saw body are mounted between the first and the second protrusion.

16. The surgical saw of claim 14 wherein:
the first stop guide and the first saw body are integral; and
the second stop guide and the second saw body are integral.

17. A surgical saw comprising:
a shaft;
a first saw blade mounted on the shaft;
a second saw blade mounted on the shaft parallel to the first saw blade;
the first saw blade having a first type tooth with a single distal tip that is bent towards the second saw blade, the first type tooth arranged in the middle of the first saw blade and the distal tip of the first type tooth aligned with a center line between two distal tips of a second type tooth having two distal tips on the second saw blade;
the first saw blade having a second type tooth on each side of the middle first type tooth on the first saw blade, the second type tooth having two distal tips;
the first saw blade having a first type tooth having one distal tip that is bent toward the second saw blade on a side of each second type tooth on the first saw blade;
the second saw blade having the second type tooth having two distal tips arranged in the middle of the second saw blade; and
the second saw blade having a plurality of teeth on either side of the middle second type tooth, the plurality of teeth alternating between a first type tooth having a single distal tip that is bent towards the first saw blade and a third type tooth having a single distal tip that is not bent.

18. The surgical saw of claim 17 wherein the middle second type tooth on the second saw blade is symmetric about the center line between the two distal tips of the middle second type tooth.

19. The surgical saw of claim 17 wherein each first type tooth and each third type tooth has a shape of an isosceles triangle.

20. The surgical saw of claim 17 wherein the first saw blade further comprises:
a saw body having a thickness;
wherein each first type tooth is on a distal end of the saw body and bent towards the second saw blade by an amount not exceeding 150% of the thickness of the saw body.

21. The surgical saw of claim 17 wherein the second saw blade comprises:
a saw body having a thickness;
wherein each first type tooth is on a distal end of the saw body and bent towards the first saw blade by an amount not exceeding 150% of the thickness of the saw body.

22. The surgical saw of claim 17 wherein the distal tip of the middle first type tooth on the first saw blade has less height than the two distal tips of the middle second type tooth on the second saw blade.

23. The surgical saw of claim 17 wherein the first saw blade further comprises third type teeth each having one distal tip that is not bent.

24. A surgical saw comprising:
a first saw blade having a first saw body having a first thickness;
a second saw blade having a second saw body having a second thickness;
a shaft having a third thickness between a first side of the shaft and a second side of the shaft; and
a retainer having a slot having a width equal to the sum of the first, second and third thicknesses;
wherein the first saw blade is mounted on the first side of the shaft and the second saw blade is mounted on the second side of the shaft; and
wherein the retainer is attached to the shaft and the first and second saw blade such that the first saw blade and the second saw blade on the first side and the second side of the shaft, respectively, fit within the slot on the retainer.

25. The surgical saw of claim 24 wherein:
the shaft further comprises a boss;
the retainer has a second slot having a thickness equal to the third thickness of the shaft; and
the boss fits within the second slot and is attached to the shaft.

26. The surgical saw of claim 25 wherein the boss has a shape selected from a group comprising a rectangular shape, a diamond shape, a circular shape, and a triangular shape.

27. The surgical saw of claim 24 wherein:
the first saw blade comprises a tang on the proximal end of the first saw blade; and
the second saw blade comprises a tang on the proximal end of the second saw blade;
wherein the retainer is attached to the shaft and the first and second saw blade such that the tang on the first saw blade and the tang on the second saw blade are mounted on the first side and the second side of the shaft, respectively, and fit within the slot on the retainer.

28. The surgical saw of claim 27 wherein:
the first saw blade has a second tang;
the second saw blade has a second tang; and
the retainer has a second slot having a width equal to the sum of the first, second and third thicknesses;
wherein the retainer is attached to the shaft and the first and second saw blade such that the second tang of the first saw blade and the second tang of the second saw blade on the first side and the second side of the shaft, respectively, fit within the slot on the retainer.

29. A method of manufacturing a surgical saw comprising:
providing a first saw blade having a first saw body having a first thickness and having teeth on a distal end of the first saw body;
providing a second saw blade having a second saw body having a second thickness and having teeth on a distal end of the second saw body;
providing a shaft having a third thickness between a first side of the shaft and a second side of the shaft;
providing a retainer having a slot having a width equal to the sum of the first, second and third thicknesses;
placing the first saw blade on the first side of the shaft;
placing the second saw blade on the second side of the shaft;
mounting the retainer on the shaft so that the first saw blade fits within the slot on the retainer and so that the second saw blade fits within the slot on the retainer with the shaft between the first and second saw blades; and
attaching the retainer to the shaft and the retainer to the first saw blade and to the second saw blade.

30. The method of claim 29 further comprising providing the shaft with a first recess on the first side of the shaft and a second recess on the second side of the shaft.

31. The method of claim 30 wherein:
the first recess has a depth equal to the first thickness of the first saw blade; and
the second recess has a depth equal to the second thickness of the second saw blade.

32. The method of claim 30 wherein providing the shaft with the first recess on the first side of the shaft and the second recess on the second side of the shaft comprises milling or grinding.

33. The method of claim 29 wherein the step of attaching comprises welding, brazing or gluing.

34. A method of forming a surgical saw comprising:
providing a shaft;
mounting a first saw blade on the shaft; and
mounting a second saw blade on the shaft parallel to the first saw blade;
the first saw blade having a first tooth having two distal tips; and
the second saw blade having a second tooth with a distal tip, the second tooth bent towards the first saw blade and the distal tip of the second tooth aligned with a centerline between the two distal tips of the first tooth.

35. A method of performing surgery, the method comprising:
using a surgical saw having a shaft, a first saw blade mounted on the shaft, a second saw blade mounted on the shaft parallel to the first saw blade, wherein the first saw blade has a first tooth having two distal tips, and
the second saw blade has a second tooth with a distal tip, the second tooth bent towards the first saw blade and the distal tip of the second tooth aligned with a centerline between the two distal tips of the first tooth.

* * * * *